US00PP08544P

United States Patent [19]

Tucker

[11] Patent Number: Plant 8,544

[45] Date of Patent: Jan. 18, 1994

[54] APPLE TREE "EVE'S APPLE"

[76] Inventor: Joseph H. Tucker, 2500 Sophia La., Kingsburg, Calif. 93631

[21] Appl. No.: 966,372

[22] Filed: Oct. 26, 1992

[51] Int. Cl.[5] ..... A01H 5/00

[52] U.S. Cl. ..... Plt./35.1

[58] Field of Search ..... Plt. 35.1

[56] References Cited

U.S. PATENT DOCUMENTS

Plt. 5421 3/1985 Hanners ..... PLT/35

*Primary Examiner*—James R. Feyrer
*Assistant Examiner*—Elizabeth C. Kemmerer

[57] ABSTRACT

This variety is distinguished from other apple tree varieties by the following principal features:

1. A dwarf habit of growth with lateral branches conducive to trellising and greater tree densities per acre.
2. A spreading spur type fruiting which enables easier picking and a large quantity per tree.
3. A larger fruit of fairly uniform size averaging 3" in diameter, that is exceptionally sweet for dessert eating or cooking.
4. This variety of "Eve's Apple" is a basically green apple with a slight blush and averaging a weight of 9 oz.

4 Drawing Sheets

BACKGROUND OF THE INVENTION

The present new and distinct variety of apple tree identified by the varietal name "Eve's Apple", was observed some distance from the inventor's orchard growing as a volunteer in the inventor's cultivated rose garden located in Porterville, Calif.

A number of plants of the present variety were asexually reproduced by bud grafting; the work was performed under a contract between the inventor and a commercial nursery namely, Sierra Gold Nurseries at 5320 Garden Highway, Yuba City, Calif. 95991 (copy of said contract enclosed). At maturity, asexual reproductions of the "Eve's Apple" variety proved to be stable and reproducible.

After 4 years of growth to a height of 11' and a spread of 8'8", I observed that this new variety could be termed as a dwarf variety with spurs at approximately every 2" along the branches. This observation was confirmed by the said nursery.

DESCRIPTION OF THE DRAWINGS

The drawings are an illustration, by photographic reproduction in color, depicting fruit of the variety; certain of such fruit being shown whole, while others are cut, horizontally and vertically, in halves with the seeds remaining in place; and depicting leaves of the variety; certain of such leaves being shown remaining on the branch, while the underneath surface of one other is shown and the upper leaf surface of the other is shown.

A detailed description of each drawing is as follows:

FIGS. 5 and 6 were taken in the Spring when buds were in bloom and the rest were taken on Aug. 18, 1992.

BOTANICAL DESCRIPTION OF THE PLANT

Figure 1:
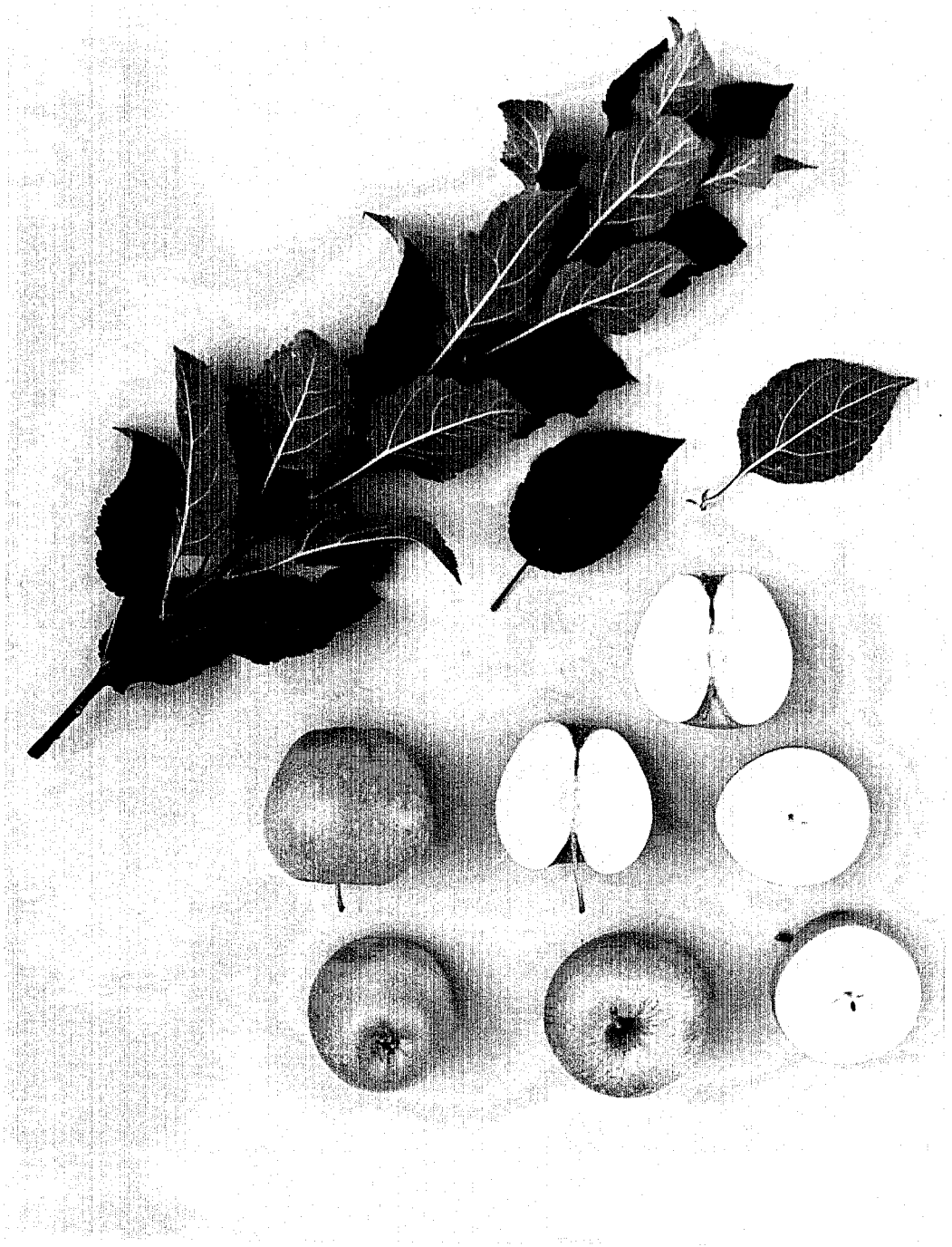
FIG. 1 Is a view of the whole mature fruit with sectional views shown vertically and horizontally cut. One branch of leaves and 2 views showing the upper and lower sides of leaves. The density of the foliage is good with 22 leaves on one foot of branch.
Figure 2:
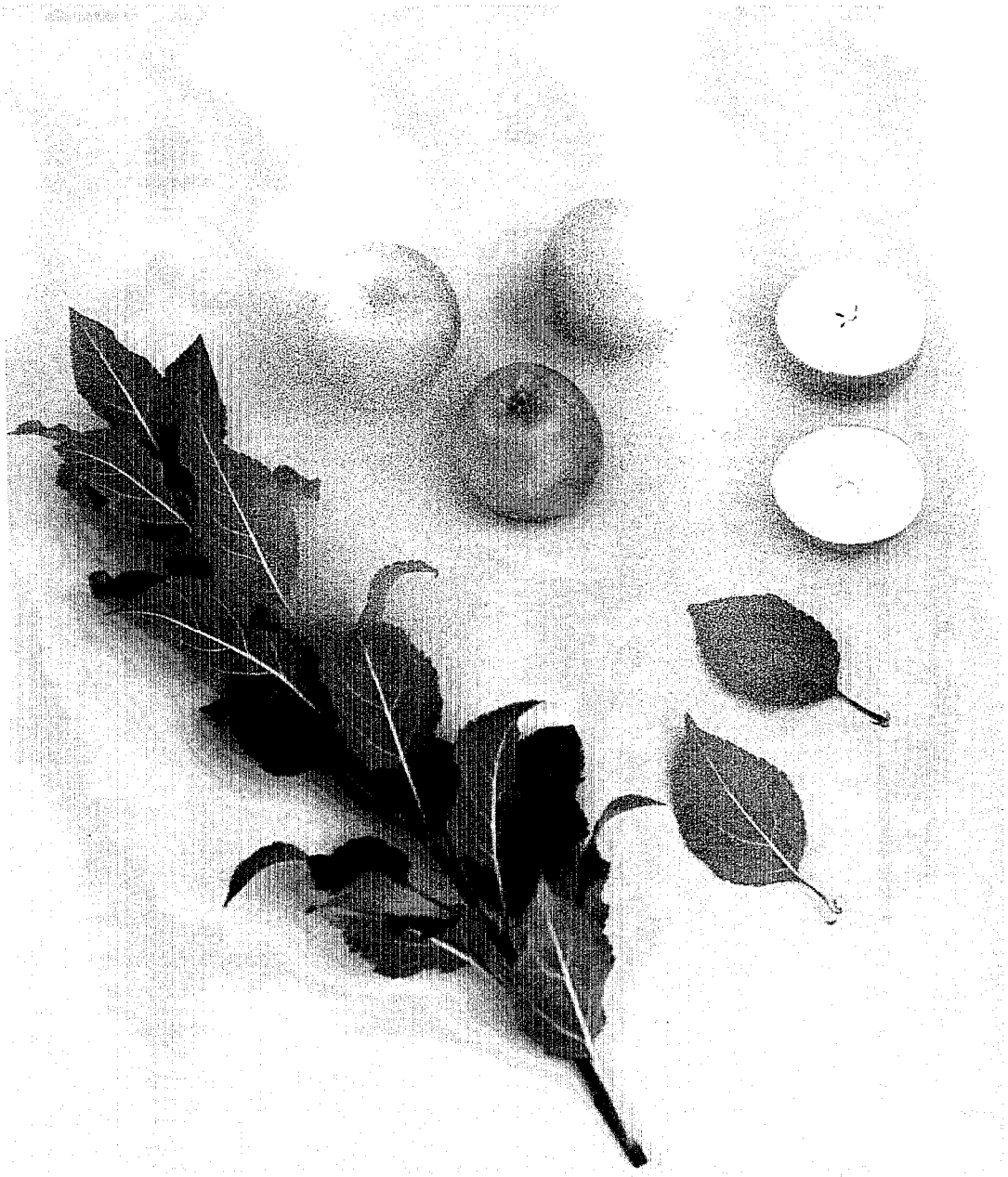
FIG. 2 Is basically the same as FIG. 1 without the vertical cross section of the fruit.
Figure 3:
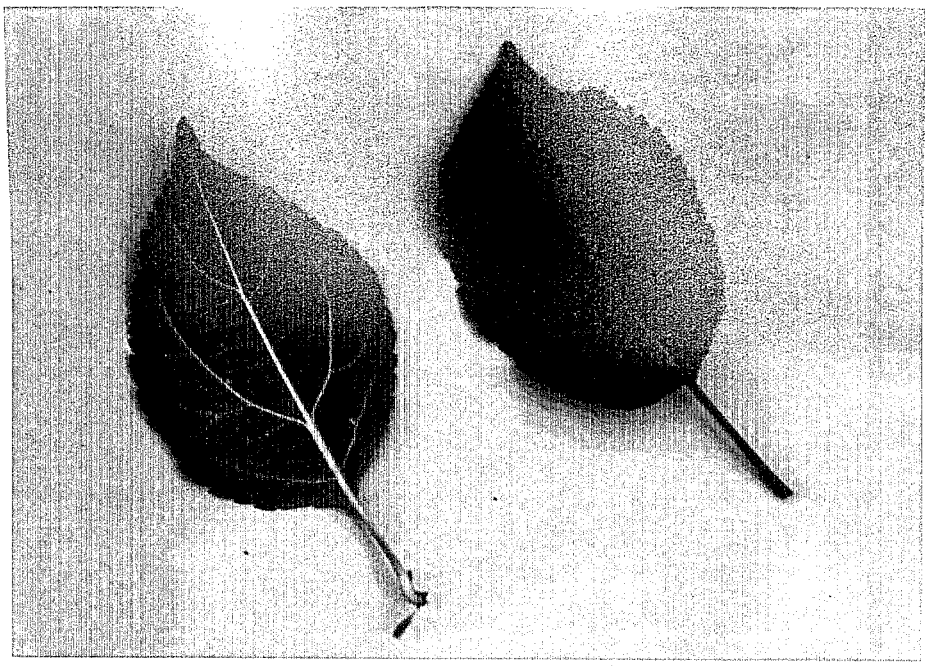
FIG. 3 A close up view of the upper and lower sides of the leaves.
Figure 4:
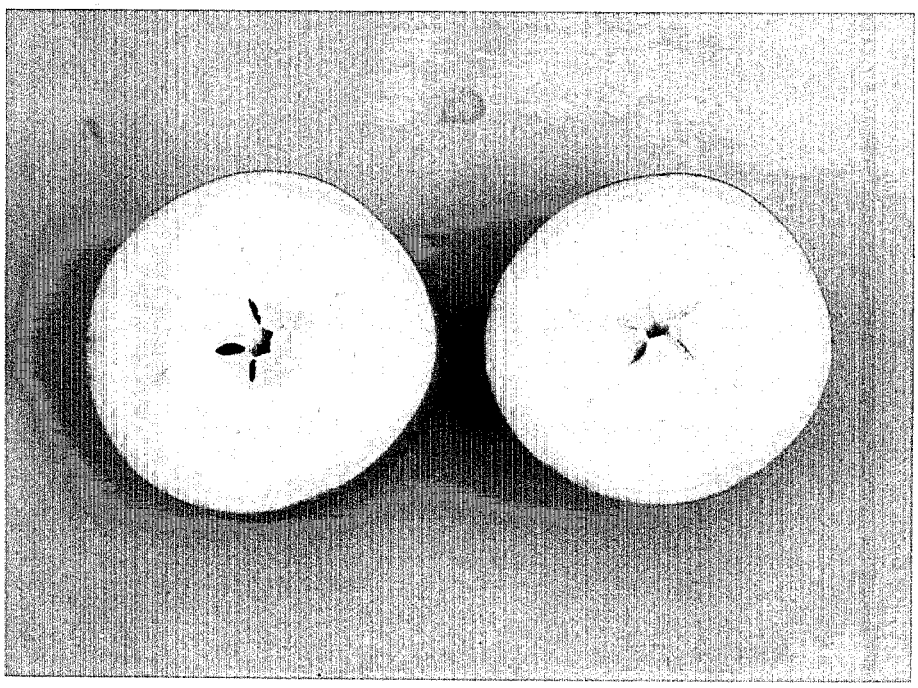
FIG. 4 A close up, horizontal cut view of the "Eve's Apple".
Figure 5:
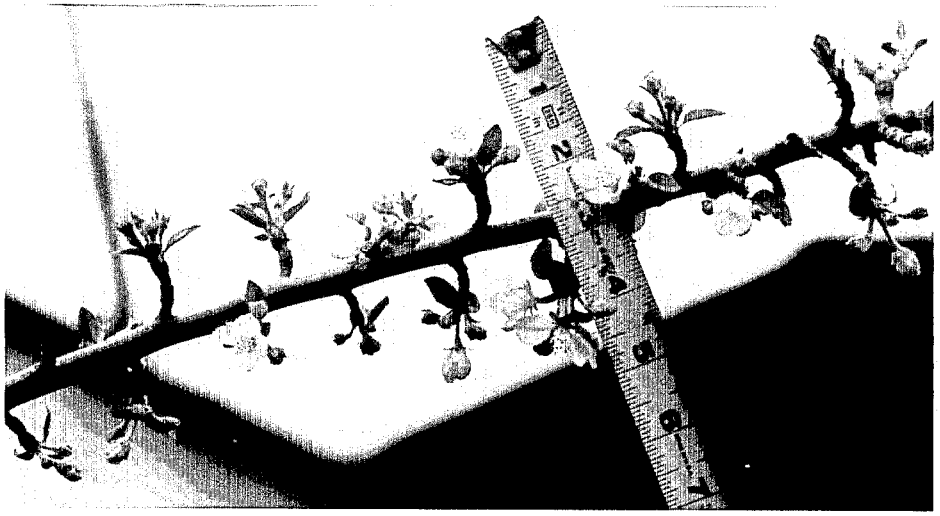
FIG. 5 Shows a branch of spurs and blossoms. A measuring tape is included for scale.
Figure 6:
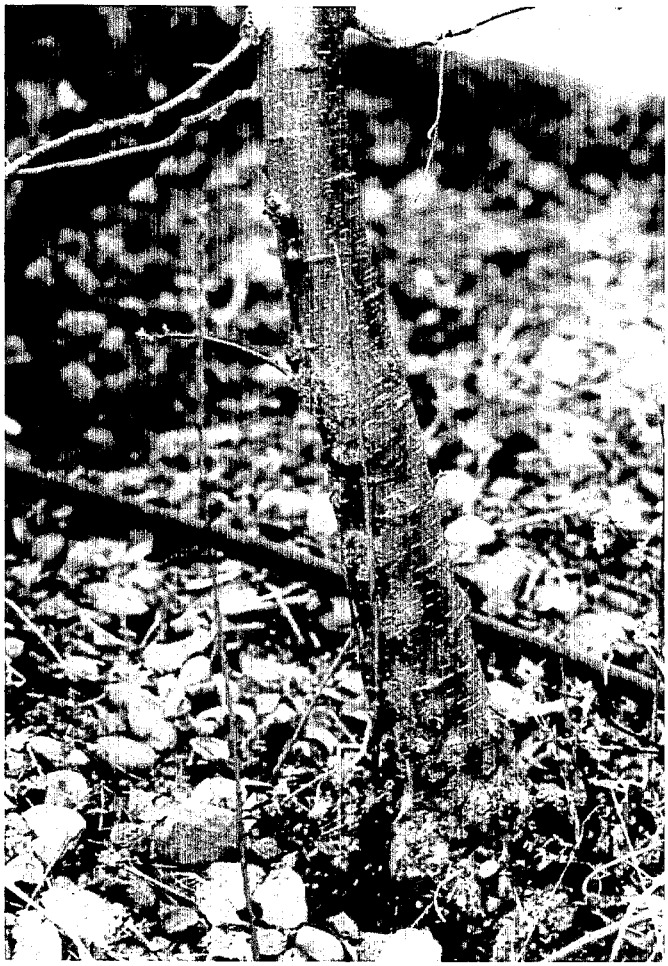
FIG. 6 Shows the base of the trunk of the "Eve's Apple" tree where it comes out of the ground and also showing a few of the lateral branches. At this showing the tree is 5 years old. This variety of the "Eve's Apple" tree grows to a height of 11' with a spread of 8'8" at maturity.

I. Classification:
- A. *Botanical classification.*—*Malus Pumila.*
- B. *Market classification.*—Early green apple.

II. Asexual reproduction:
- A. *Mode.*—Bud grafting.
- B. *Location.*—5320 Garden Highway, Yuba City, Calif. 95991.
- C. *Rootstock.*—Seedling.

III. Discovery or development:
- A. *Newly found seedling.*—1. Parentage: Not known. After eating an apple, I planted some of the seeds in my rose garden in the Fall 1986. When seedlings appeared I took particular interest. It had its 1st fruit in 1989 and I noted it had a different taste. It was also noted to be a dwarf and spur type variety. The nearest apple trees were Granny Smiths some 269 feet away. 2. Where discovered: a. Among what type of planting? The fruit tree was found in a rose garden on my farm in Porterville, Calif. b. Who owned property at time of discovery? Joseph H. Tucker. 3. When discovered: In the Spring of 1987 the seedling was discovered and in the Summer of 1989 it gave its first fruit. 4. By whom discovered: The fruit tree and fruit was discovered by Joseph H. Tucker. 5. Pollination and thinning requirements: When tree was in bloom, own fruit, a pollinator would be advantageous. Since this variety is a heavy producer, thinning is required.

IV. Reproduction:

A. *How.*—Bud wood taken from the parent tree and grafted onto root stock.

B. *Where.*—The work was done at 5320 Garden Highway, Yuba City, Calif. 95991-9499.

C. *By Whom.*—Sierra Gold Nurseries.

V. Most significant features: This is a dwarf spur tree with horizontal branches which makes it perfect for trellising.

VI. Description: (Tree).

A. *Size.*—Dwarf.

B. *Figure.*—Upright, Horizontal branching tendency.

C. *Productivity.*—Very productive.

D. *Regularity of bearing.*—Consistent bearing.

E. *Trunk.*—1. Diameter in relation to length: 2½" diameter, 30" high. 2. Surface characteristics: Smooth.

F. *Branches.*—1. Size: Medium. 2. Surface character: Smooth. 3. Color: Plate 15, Page 53, A-2, Traprock+Seabird−. 4. Lenticels: a. Number: Numerous. b. Size: 0.1–0.4 mm.

G. *Leaves.*—1. Size: Medium: 2. Length: 80–85 mm. 3. Width: 50–55 mm. 4. Shape: Ovate with point 5. Color: Upper Leaf: Plate 23, Page 69, H-9, Meadowgrass. Lower Leaf: Plate 23, Page 69, H-7,, Cypress Green+Forest−. 6. Marginal Form: Double Serrated. 7. Glandular Characteristics: None. 8. Petiole: a. Length: 32–35 mm. b. Thickness: 2 mm. 9. Stem Glands: N/A. 10. Stipules: N/A.

VII. Flower buds:

A. *Size.*—7 mm.

B. *Shape.*—Small, plump and roundish.

C. *Surface.*—Glabrous.

D. *Other distinguishing characteristics.*—5 Carpels.

E. *Color.*—White with deep rose blush.

VIII. Flowers:

A. *Date of first bloom.*—Unknown. Bloom time not noted prior to 1992. For 1992 season bloom time noted to be March 8.

B. *Size.*—Small; 12–15 mm.

C. *Petals.*—5.

D. *Stamens.*—17–20, Average 18.

E. *Pistil.*—1.

IX. Fruit:

A. *Maturity.*—Ready for picking from July 15–20.

B. *Size.*—1. Uniformity: Fairly uniform. 2. Diameter: 78–85 mm. 3. Transverse in axis: 73–80 mm. 4. Transverse at Right Angles to axis: N/A.

C. *Form.*—1. Uniformity: Viewed from top or stem — round. Viewed from side — conic. 2. Symmetrical or Asymmetric: Symmetrical. 3. Suture: N/A. 4. Stem Cavity: Acute; 24–29 mm wide by 15–19 mm deep. 5. Base: Wide and sloping; calyx is open and recurved. 6. Apex: Wide 35 mm. 7. Calyx: Depressed. 8. Stem: a. Length: Long; 34–37 mm. b. Caliper: 3 mm. 9. Skin: a. Thickness: Medium. b. Texture: Minimal texture to smooth. c. Tendency to crack: not observed. d. Color: Base: Plate 17, Page 57, J-3, Sea-foam Y Blush: Plate 4, Page 31, G-10 , Araby covering approximately 15% of skin surface in Tulare County climate. e. Surface bloom: Not observed.

D. *Flesh.*—1. Color: Plate 10, Page 43, B-1, Oyster White+. 2. Juice: Slight juice. 3. Flavor: Extremely sugary with minimum apparent subacid. 4. Aroma: Slight. 5. Texture: Fine. 6. Ripening (even or uneven and where first): Even. 7. Eating quality: Very Good to Excellent.

E. *Core.*—1. Position: Sessile. 2. Seed Cells: Closed. 3. Core line: Relative Small; width much greater than height meeting in cross section, indistinct.

F. *Seed length.*—8 mm. Seed width. 5 mm. Seed form, acute. Typical seed count: 5 per fruit all perfect, one per cell. Color: Plate 7, Page 37, J-12, Chutney.

G. *Ripening characteristics.*—All the fruits ripen evenly, individually, and on the tree.

H. *Use.*—Eating and cooking.

I. *Keeping quality.*—Good. To simulate commercial cold storages, apple was sealed in a plastic bag and stored in the home refrigerator. After 6 months under these conditions, the keeping quality was very good. After initial ripening the apple can be kept on the tree for up to 4 weeks.

J. *Shipping quality.*—Good.

K. *Water core.*—Not observed.

X. Resistance to disease: Slight tendency to bitter pit.

XI. Has the new variety been sold?: No.

XII. Has the new variety been publicly used or exhibited?: No.

XIII. Have any reproducible parts of the plant been given away?: No.

XIV. Has the new variety been given a name?: Yes, "Eve's Apple".

Dictionary of Color: A. Maerz and M. Rea Paul. McGraw-Hill Book Company, Inc. New York, N.Y. Second Edition 1950.

Date Complied by: Dr. Allan A. Hewitt, Ph.D. Agricultural Consultant. Professor of Horticulture, Emeritus. California State University, Fresno. Fresno, Calif. 93740.

I claim:

1. The new and distinct variety of a Dwarf Spur Apple Tree named "Eve's Apple" as described and illustrated herein.

* * * * *

UNITED STATES PATENT AND TRADEMARK OFFICE

CERTIFICATE OF CORRECTION

PATENT NO. : PP 8,544

DATED : January 18, 1994

INVENTOR(S) : Tucker

It is certified that error appears in the above-indentified patent and that said Letters Patent is hereby corrected as shown below:

Column 2, line 46, after "when tree was in bloom" insert --I experimented by placing a covering around a few blooms to see if they were self pollinating. Apples did form on the covered blooms but not in the same quantity as the uncovered branches. I gather from this that though the tree sets its --.

Signed and Sealed this

Twenty-fifth Day of October, 1994

*Attest:*

Bruce Lehman

BRUCE LEHMAN

*Attesting Officer*

*Commissioner of Patents and Trademarks*